(12) United States Patent
Czeizler

(10) Patent No.: US 6,284,260 B1
(45) Date of Patent: *Sep. 4, 2001

(54) TREATMENT WITH ERYTHROPOIETIN OF BLEEDING FROM BENIGN AND MALIGNANT LESIONS WITH NORMAL AND ABNORMAL COAGULATION PARAMETERS

(76) Inventor: Veronica L. Zaharia Czeizler, 237 E. 20th St., New York, NY (US) 10003

( * ) Notice: Subject to any disclaimer, the term of this patent is extended or adjusted under 35 U.S.C. 154(b) by 0 days.

This patent is subject to a terminal disclaimer.

(21) Appl. No.: 09/335,077

(22) Filed: Jun. 17, 1999

Related U.S. Application Data

(63) Continuation-in-part of application No. 09/018,815, filed on Feb. 4, 1998, now Pat. No. 5,951,996
(60) Provisional application No. 60/091,598, filed on Jul. 2, 1998, and provisional application No. 60/125,253, filed on Mar. 19, 1999.

(51) Int. Cl.$^7$ .............................. A61F 2/02; C07K 14/505
(52) U.S. Cl. ............................................ 424/423; 530/350
(58) Field of Search .............................. 424/423; 530/350

(56) References Cited

U.S. PATENT DOCUMENTS 5,554,380 * 9/1996 Cuca .................................... 424/441
5,951,966 * 9/1999 Czeizler .............................. 424/423

* cited by examiner

*Primary Examiner*—Carlos A. Azpuru
(74) *Attorney, Agent, or Firm*—Gottlieb, Rackman & Reisman, P.C.

(57) ABSTRACT

A method for the treatment of bleeding from organs involved with benign and malignant lesions by the subcutaneous administration of Erythropoietin. The method makes unnecessary the need for surgery or transfusion of large amounts of blood. The invention provides a conservative treatment for bleeding which works on extensive areas of benign lesions and malignant lesions. The treatment has the following benefits: (1) stops bleeding, (2) eliminates the need for further transfusions, with its attendant complications, (3) allows for treatment as an outpatient, (4) eliminates the need for surgery, (5) allows the patient to return to an excellent quality of life, (6) has no observed side effects, (7) stops bleeding while the patient is fully anti-coagulated, and (8) treats benign and malignant bleeding lesions. Patients with normal or abnormal coagulation/ hemostasis can benefit from the hemostatic benefits of Erythropoietin.

20 Claims, No Drawings

TREATMENT WITH ERYTHROPOIETIN OF BLEEDING FROM BENIGN AND MALIGNANT LESIONS WITH NORMAL AND ABNORMAL COAGULATION PARAMETERS

This application is a continuation-in-part of Ser. No. 09/018,815, filed Feb. 4, 1998, and now U.S. Pat. No. 5,951,996 claims priority of provisional applications Nos. 60/091,598 filed Jul. 2, 1998, and 60/125,253 filed Mar. 19, 1999.

FIELD OF THE INVENTION

This invention relates to a novel use for the pharmaceutical compound Erythropoietin. The invention further relates to methods for controlling bleeding of the gastro-intestinal tract, uterine cavity, nasal cavity (cavitary organs) as well as the prolonged bleeding of incompletely/improperly healed surgical wounds as well as from any organ or body part involved with benign or malignant lesions.

BACKGROUND OF THE INVENTION

Bleeding from benign and malignant lesions in patients being naturally or therapeutically anti-coagulated or having other hemostatic abnormalities is a serious medical problem. Below are some challenging clinical conditions associated with recurrent bleeding with no satisfactory treatment conservative or surgical. It is in these and other conditions that Erythropoetin helps to control the bleeding. Diffuse GI (gastrointestinal) bleeding is a major medical problem following radiation treatments. Angiodysplasia of the intestine is now considered the most frequent cause of major colorectal bleeding being more frequent with diverticular bleeding. Radiation proctosigmoiditis has been studied by Gilinsky et. al. (1983) who found that 35% of patients had moderate GI bleeding and 20% had appreciable bleeding with a significant number of these patients needing operation to remove the affected bowel segment.

Patients suffering from diffuse GI bleeding are currently treated with repeated blood transfusions and surgical resection of the involved segment of the GI tract. A major problem with surgical treatment, however, is that a bowel that has been irradiated does not heal well and the breakdown of a suture line after surgery is a frequent complication, requiring further surgery and the removal of more of the bowel. Also, the dense adhesions that developed following radiation to the pelvis often make it difficult to delineate normal anatomy from pathology, and surgery therefore results in the removal of more bowel than is strictly necessary. Sometimes, it is difficult to establish the exact site of bleeding. Sometimes, the small and large bowel are affected concomitantly and establishing the exact extent of re-section can be very difficult for the surgeon.

Colonoscopic electro-coagulation and laser therapy are the preferred method of treatment for recurrent bleeding. The incidence of re-bleeding and the need for repeating the procedure varies from 0–34%. Surgical resection is often necessary when bleeding recurs. Occasionally re-bleeding occurs post-resection when the site of bleeding is more extensive that originally thought. In both situations presented, there is a need for a conservative treatment which should work on extensive areas of the GI mucosa.

Conservative treatment (steroid retention enemata) by administration of sulphasalazine and 5-aminosalicylic acid (mesalamine—a gastrointestinal anti-inflammatory used in the treatment of ulcerative colitis) has been tried with variable results. In cases of angiodysplasia of the intestine, the use of vasopressin infusions lead to re-bleeding in 21% of cases. Embolisation with Gelfoam has a high risk of re-infarction. These attempts at conservative treatments demonstrate that there has been a long felt need for an alternative to surgical intervention to reduce diffuse GI bleeding.

Erythropoietin (also known as procrit or Epo) is a glycoprotein hormone, thought to be produced primarily in the kidneys and to a lesser extent in the liver, which is a stimulating factor for erythropoiesis, the process by which erythrocytes (red blood cells) are formed. Human erythropoietin has been produced by recombinant technology, and is known as Epoetin.

Erythropoietin is being used successfully in the treatment of anemia of chronic renal failure, anemia of cancer and in HIV patients. It is primarily used to induce production of red blood cells to combat anemia, and not to restrain diffuse bleeding. A recent study pointed towards the usefulness of Erythropoietin in the treatment of GI malignancies but it only pointed its red blood cell stimulating effect leading to improvement of the anemia and did not refer/recognize at all at its hemostatic effect (stopping the GI blood loss). Erythropoietin is known to decrease the bleeding time in uremic (kidney failure) patients. In vitro and in vivo studies have shown an improved platelet endothelial cell interaction, which explains the shortening of the bleeding time. But there has been no recognition prior to the present invention of the significant limitation of GI bleeding that can be achieved by the administration of Erythropoietin.

There are three reported cases of Jehovah's witnesses patients who had acute as opposed to chronic blood loss with critically low Hgb. The patients refused blood transfusions and were successfully treated with recombinant Erythropoietin plus ferrous sulfate, folic acid and vitamin B-12 subcutaneously.

One patient was a 66 year old woman who bled from multiple peptic ulcers. She had melena (passing of black bloody bowel movement) and sycope (passing out) with a Hcrt of 14.5%. Since she refused blood transfusion she was treated with recombinant Erythropoietin 20,000 units for three doses followed by 6,500 units up to two weeks. On the 14th day, her Hcrt was 27.1%. The Erythropoietin was not administered to contain bleeding, but was administered to increase the hematocrit count by boosting the red cell production only after the bleeding had stopped. Furthermore there's nothing in the publication, "Erythropoietin and Anemia of Gastrointestinal Bleeding in a Jehovah's Witness", Ann. Int. Med. 112, 552 (April 1990), that indicates that erythropoietin would stop diffuse GI bleeding. The thrust of the publication is the use of Erythropoietin as a substitute for blood transfusion for Jehovah's Witnesses.

The second case was a four year old black male Jehovah's witness with hematemesis (vomiting of blood) who was found to have a 2.5 cm fundal ulcer and a Hcrt of 19.1. He was treated with Fe Dextran IV 100 mg/day, Erythropoietin 50 units/kg IV. On the 8th day, his Hcrt was 22.9 and he was discharged home.

The third and last case presented in the literature was a 14 year old black male who had massive hematemesis (vomiting of blood) following esophageal dilatation for an esophageal stricture. Being a Jehovah's witness, blood transfusion was refused. He underwent surgical repair for Gastroesofphageal tear. The post-operative Hcrt was 14.4. Recombinant Erythropoietin 50 units/kg IV was given. Four days after surgery, his Hcrt was 25.9 and was discharged home on the 9th post-operative day tolerating oral feeding and oral iron supplementation.

Erythropoietin beta has been used successfully in the treatment of advanced gastrointstinal cancer, but only to increase haemoglobin/hematocrit (Hgb/Hcrt) by stimulation of red blood cell production. Its effect on stopping gastrointestinal bleeding was not recognized in that context ("Erythropoietin Beta in the treatment of anemia in patients with advanced gastro intestinal cancer") J. Clin. Oncology 16, No. 2 (February 1998) p. 434–40).

In uremic patients, it is known that erythropoietin corrects the prolonged bleeding time after one week of treatment and increases the hemoglobin/Hcrt after two weeks of treatment. But this information has not been previously considered related to the problem of GI bleeding in uremic or non-uremic patients. An enhanced platelet aggregation in response to ristocetin was noted and, in erythropoietin treated patients, correlated with the rise in platelet serotonin. A decrease in protein C & S and Antithrombin III was noted, leading to shortening of the bleeding time. These results pointed towards an improved platelet vessel wall interaction possibly via a serotoninergic mechanism.

BRIEF DESCRIPTION OF THE INVENTION

In patients with bleeding from benign or malignant lesions from any body part or organ (angiodysplasia of the colon, radiation proctitis, rectal cancer, endometrial cancer, epistaxis (bleeding from the nasal cavity), in a patients naturally or therapeutically anticoagulated , or in a patient with other hemostatic defects the treatment of the present invention comprises administration of Erythropoietin, preferably subcutaneously. The invention results in the increase of hemoglobin/hematocrit (Hgb/Hcrt) and no further need for transfusion. Continuation of the administration of Erythropoietin at much lower than initial doses at weekly intervals for several months is necessary to avoid re-bleeding and a drop in Hgb/Hcrt.

In the nine examples presented below, recombinant Erythropoietin (1) stopped the bleeding, (2) no further transfusions were needed, thereby avoiding the complications of repeated transfusions, (3) treatment was as an outpatient (4) without the need for surgery, (5) the patient returned to an excellent quality of life, (6) there was a major saving to the health industry, and (7) no side effects were noted.

The present invention therefore provides a conservative treatment which works to reduce severe bleeding in benign and malignant lesions in patients with normal and abnormal hemostasis.

DETAILED DESCRIPTION OF A PREFERRED EMBODIMENT

The invention is appropriate for patients suffering from severe bleeding from benign and malignant lesions and improperly healed surgical wound, and some of these patients having abnormal hemostasis. Treatment with recombinant Erythropoietin is initiated for the purpose of stopping the bleeding, boosting the red blood cell production and decreasing future transfusion requirement, at the dose of 5,000 units, three times per week or higher doses depending on the severity of bleeding or of the anemia. When Hgb/Hcrt is stable for several days and there is no further clinical evidence of ongoing bleeding, the patient may be discharged on maintenance doses of recombinant Erythropoietin which varies from patient to patient from 2,000 units, once a week to same dose every two weeks up to 10,000 units three times a week. After a few weeks of lack of recurrence of bleeding, the patient is placed on 3000 units of recombinant Erythropoietin injection at once a week. After treatment is initiated in accord with this invention no further transfusion is needed, although bleeding may recur, some drop in Hgb/Hcrt may occur, if Erythropoietin treatment is dropped completely, but with complete resolution of these symptoms if Erythropoietin is restarted.

EXAMPLE 1

A 65 year black male was treated in accord with the present invention. The patient had a history of radiation proctitis secondary to radiotherapy for a prostate cancer with a string of hospital admissions for critically low Hgb/Hcrt and packed RBC transfusions prior to the initiation of erythropoietin. When first seen in consultation during one of his hospital admissions, when his Hgb was 3.5, Hcrt-12.2 and MCV 65. During the 6 weeks preceding the initiation of Erythropoietin, 20 units of PRBC were transfused. A repeat colonoscopy revealed diffused angioectasia (dilation of the small blood vessels) of the recto-sigmoid mucosa and diffused erosions and oozing of blood, consistent with radiation proctitis. Courtenemas were unsuccessful in stopping the bleeding. Recombinant erythropoietin 5,000 units three times a week were started. After the first week of treatment, the bleeding completely stopped. No further transfusion was needed, the patient's bleeding stopped and he felt better. The patient was however very non-compliant to continuing the treatment. Eventually his Hgb came up to 13 and he returned. The patient would come once every one-two weeks and later on every three weeks at which time recombinant Erythropoietin 5,000 units were administered subcutaneously. During the time when he was off-recombinant Erythropoietin for several weeks, his Hgb would drop to about 7.0 and he had rectal bleeding. After recombinant Erythropoietin was restarted , the rectal bleeding would disappear and the Hgb/Hcrt would rise. To this date, no packed RBC were transfused after Erythropoietin had been started. No side effects were noted.

EXAMPLE 2

Another patient was an 88 years old with multiple hospital admissions for lower GI bleeding and severe symptomatic iron deficiency anemia. For the previous two years he was admitted every two months for packed red blood cell transfusion of 4 units. He was seen in consultation in Mar. 1997 (when he was admitted for hematochesia a Hgb of 9.0 and colonoscopy revealed diffuse colonic angiodysplasia.). He was started on recombinant Erythropoietin 4,000 units three times a week which he received for two weeks, followed by 4,000 units two times a week for two months after which he was maintained on 2,000 units once or twice a week, then 3000 units once a week.

His Hgb has increased from 9.0 to 13.0. He was very compliant with respect to treatment and no transfusion of packed red blood cells has been used since recombinant erythropoietin was initiated. His Hgb was between 12.0 and 13.0 for the subsequent year with no clinical evidence of bleeding. No side effects were noted.

EXAMPLE 3

Is a 69 year old female with a history of rectal cancer who had resection of the tumor followed by chemotherapy and radiotherapy with a history of several weeks of rectal bleeding. Five and a half months ago her Hgb/Hcrt were 6.9/20.9 and she was transfused 2 units of PRBC. Two weeks later, her Hgb/Hcrt were 7.7/24.6 and 4 units of PRBC were transfused. Ten days later, she was transfused another 2 units of PRBC. rHuEPO 5,000 units subcutaneously for 3 days were started while in the hospital after which she was discharged home. As an outpatient, she came to the office every 1–2 weeks for chemotherapy with 5 FU and Leucovorin. At which time she received rHuEPO 2,000 units subcutaneously. The rectal bleeding stopped completely after the third dose of rHuEPO. Two months later, the patient was transfused 2 units of PRBC. The very low dose of rHuEPO 2,000 units every 1–2 weeks kept the patient free of transfusion for 7 weeks. Whereas during the months prior to starting rHuEPO, 8 units of PRBC were transfused. It is presumed that higher doses would have had the patient entirely transfusion free. No side effects were noted.

EXAMPLE 4

Is a 74 year old female with a one and a half year old history of vaginal bleeding. She was diagnosed to have adenocarcinoma of the endometrium. Since laparoscopy revealed omental and liver metastasis, hysterectomy was not performed. Post-operatively, she developed deep venous thrombosis of the left femoral vein for which she was treated with therapeutic doses of heparin and later on coumadin (both anti-coagulants). The patient also received chemotherapy (Cisplatinum,Adriamycin, and 5 FU) combined with radiotherapy. She was discharged from the hospital with a Hgb of 9 with active vaginal bleeding and on therapeutic doses of coumadin. rHuEPO subcutaneously was started 2,000 units 3 times per week. During the second week of rHuEPO treatment, the vaginal bleeding stopped and her Hgb remained stable at 9.5 for the following 3 months after which she was lost to follow-up. No side effects were noted.

EXAMPLE 5

Is a patient with end-stage renal disease on hemodialysis, liver insufficency due to cirrhosis of the liver with a PT and PTT one and a half times the normal for many months. He developed severe epistaxis for which he was admitted to the hospital. Nasal packing was done. But after removal of the packing the bleeding continued. The patient was for a long time on 10,000 units of recombinant rHuEPO given intravenously 3 times a week for chronic anemia. In view of the continued bleeding, the rHuEPO was increased from 10,000 units 3 times a week intravenously to 15,000 units daily subcutaneously. Twenty-four hours later, the epistaxis completely stopped and remained so for the following week. Later on, rHuEPO was decreased to his original dose of 10,000 units 3 times a week given intravenously without recurrence of bleeding and was discharged home. No side effects were noted.

EXAMPLE 6

Is a 67 year old female with a history of breast cancer in remission for several years on Tamoxifen. She underwent by-pass surgery for arteritis of the left lower extremity. She is on anti-coagulation for a chronic atrial fibrillation. Several weeks following her surgery, the surgical wound was still not closed and a sero-sanguinous discharge was slowly leaking from the open wound. rHuEPO 2,000 units subcutaneously 2 times a week led to decreased and then complete resolution of the fluid. rHuEPO was stopped. Surgical manipulation of the improperly/incompletely closed surgical incision site led to recurrence of bloody fluid leakage. Restarting the rHuEPO treatment at the same dose as before led to a decreased oozing of the bloody fluid. No side effects were noted.

EXAMPLE 7

Is an 84 year old male with recurrent bleeding due to angiodysplasia of the colon, requiring multiple hospital admissions and blood transfusions despite oral iron supplementation. After being started on outpatient rHuEPO, his stools became free of blood and no transfusion of PRBC was required over the ensuing 18 months. On a maintenance dose of 4,000 U/week and later on 4,000 U every 2–3 weeks, his Hgb remained stable at around 12. No side effects were noted.

EXAMPLE 8

Is an elderly female with recurrent melena due to angiodysplasia of the duodenum. The patient was therapeutically anticoagulated for a valvular heart disease. Despite oral iron supplementation and repeated endoscopic attempts to stop the bleeding she required frequent PRBC transfusions. Following multiple transfusions, the patient developed an autoimmune hemolytic anemia, and her transfusion requirements increased. After rHuEPO was started her stools became negative for occult blood and repeat endoscopies failed to show any bleeding. She was maintained on rHuEPO, 30,000 U/week. No side effects were noted.

EXAMPLE 9

Is a 69 year old patient on therapeutic anticoagulation for a valvular heart disease, who underwent revision of an occluded femoropopliteal bypass graft. Two weeks postoperatively the would was still not healed and was bleeding. RHUEPO at a mean dose of 6,000 U/week stopped the bleeding in one week. No side effects were noted.

The nine examples showed a clear benefit in using recombinant Erythropoietin to stop bleeding from benign and malignant lesions some of these patients having normal and some abnormal coagulation/hemostatic parameters. The effectiveness of rHuEPO in stopping severe parenchymal bleeding is made obvious by its effect while the patient is under treatment and restarting bleeding when the treatment is interrupted. Also, its effect in stopping bleeding in patients anti-coagulated naturally/therapeutically or with other hemostatic abnormalities, obviates its clinical benefit. rHuEPO provides a conservative treatment for bleeding conditions for which there was no good treatment, conservative or surgical. Patients who were completely transfusion dependent become totally transfusion independent. The patients who needed admission for their bleeding were started on rHuEPO in the hospital and were discharged shortly thereafter to continue their treatment as an outpatient. None of the patients needed surgery in order to stop bleeding, the patients returned to an excellent quality of life, there was a major saving to the health industry, and no side effects were noted. This new use of recombinant Erythropoietin beyond the anemia of chronic renal failure, anemia of HIV infected patients, anemia of cancer provides a new significant medical treatment.

The present invention also has application to the treatment of bleeding benign and malignant pulmonary parenchymal lesions. In general, in view of the present discoveries, rHuEPO should be considered for its hemostatic properties extending beyond its present indication for boosting hemopoesis.

Although the invention has been described in terms of preferred embodiments and specific examples, it is expected that the invention may be practiced by modifications that persons skilled in this art may achieve. Accordingly the invention is to be understood as what is described in the following claims.

I claim:

1. A method for treating bleeding from various organs involved with benign and malignant lesions in patients with normal and abnormal coagulation/hemostatic parameters, comprising administering to an individual in need of said treatment effective doses of Erythropoietin so that the symptoms of bleeding are significantly reduced.

2. The method for treating bleeding from organs involved with benign and malignant lesions of claim 1 in which the dose of Erythropoietin is administered in the form selected from the group consisting of Erythropoietin and recombinant Erythropoietin.

3. The method for treating bleeding of claim 2, in which the Erythropoietin is administered in dosages between 15,000 to 105,000 units per week until the bleeding stops, and continuing to administer Erythropoietin on a reduced basis thereafter.

4. The method for treating bleeding of claim 2, in which the Erythropoietin is administered subcutaneously in dosages up to 105,000 units per week until the bleeding stops, and continuing to administer Erythropoietin on a reduced basis thereafter.

5. The method for treating bleeding of claim 3, wherein the continued administration of Erythropoietin takes place weekly or biweekly.

6. The method for treating bleeding of claim 1, wherein the bleeding is a result of radiation induced proctitis, diffused angiodysplasia of the colon, rectal cancer, uterine cancer, epistaxis, incompletely/improperly healed surgical suture line, angiodisplasia of the gastrointestinal tract, or retroperitoneal bleeding or bleeding from any organ or body part.

7. A method for treating bleeding in a patient suffering from severe GI bleeding with critically low Hgb/Hcrt comprising administering to an individual in need of said treatment and effective dose of Erythropoietin so that the Hgb/Hcrt is stable for several days and there is no further clinical evidence of ongoing bleeding, and discharging the patient on maintenance doses of recombinant Erythropoietin.

8. The method of treating bleeding of claim 1, in which the administration is subcutaneous, intravenous, or oral.

9. The method for treating bleeding of claim 1, in which the amount administered is a dose of approximately 15,000 to 105,000 units per week.

10. The method for treating bleeding of claim 1, in which the maintenance dose is approximately 2,000–15,000 units per week, or other doses that maintain a stable Hemoglobin.

11. The method for treating bleeding of claim 1, comprising the further step of placing the patient on dosages of recombinant Erythropoietin injection of 4,000 to 24,000 units per month.

12. The method for treating bleeding of claim 1, comprising the further step of placing the patient on dosages of recombinant Erythropoietin injection adjusted in order to maintain a stable Hemoglobin.

13. The method for treating bleeding of claim 1, comprising the further step of placing the patient on dosages of recombinant Erythropoietin injection of approximately 50,000 units per month.

14. The method for treating bleeding of claim 1, wherein the amount administered is a dose of approximately 15,000 to 105,000 units per week, the maintenance dose is 4,000–105,000 per week, and the patient is subsequently placed on dosages of recombinant Erythropoietin injection at approximately 1, 2, 4 weeks interval.

15. The method for treating bleeding of claim 1, wherein the amount administered are doses that maintain a stable Hemoglobin and the patient is free of signs of bleeding.

16. The method for treating bleeding of claim 1, in patients having benign as well as malignant lesions are being treated by administration of rHuEPO for the purpose of stopping the bleeding.

17. The method for treating bleeding of claim 1, in which patients who have normal coagulation parameters as well as abnormal coagulation parameters (due to liver failure or therapeutic anti-coagulation) or who have normal or abnormal hemostasis, are being treated with rHuEPO for the purpose of stopping ongoing bleeding.

18. The method of treating bleeding of claim 1, in which patients already on 10,000 units of rHuEPO intravenously 3 times a week are being treated with 15,000 units of rHuEPO daily subcutaneously for the purpose of stopping bleeding, after the bleeding completely stopped, they can be switched back to their original dose of 10,000 units of rHuEPO given intravenously 3 times a week.

19. The method for treating bleeding of claim 7, wherein said patient is suffering from angiodysplasia of the colon, radiation proctitis, rectal cancer, uterine bleeding, epistaxis, incompletely or improperly healed surgical suture line, retroperitoneal bleeding, angiodysplasia of the gastrointestinal tract, or any other benign or malignant lesion from any organ or body part.

20. The method for treating bleeding of claim 14, wherein said malignant lesions originated from the rectum, the uterine cavity or any other organ.

* * * * *